(12) United States Patent  (10) Patent No.: US 9,271,703 B1
Dickinson  (45) Date of Patent: Mar. 1, 2016

(54) ANESTHESIA DELIVERY DEVICE

(71) Applicant: Jon Alan Dickinson, San Rafael, CA (US)

(72) Inventor: Jon Alan Dickinson, San Rafael, CA (US)

(73) Assignee: Jon Alan Dickinson, San Rafael, CA (US)

( * ) Notice: Subject to any disclaimer, the term of this patent is extended or adjusted under 35 U.S.C. 154(b) by 0 days.

(21) Appl. No.: 14/544,197

(22) Filed: Dec. 8, 2014

(51) Int. Cl.
| | |
|---|---|
| *A61M 5/00* | (2006.01) |
| *A61B 17/00* | (2006.01) |
| *A61M 39/08* | (2006.01) |
| *A61B 17/34* | (2006.01) |
| *A61M 39/12* | (2006.01) |

(52) U.S. Cl.
CPC ....... *A61B 17/00008* (2013.01); *A61B 17/3478* (2013.01); *A61M 39/08* (2013.01); *A61M 39/12* (2013.01); *A61B 2017/00477* (2013.01); *A61B 2017/00486* (2013.01); *A61B 2017/347* (2013.01)

(58) Field of Classification Search
CPC .......... A61M 25/007; A61M 25/0097; A61M 25/0082; A61M 25/0147
USPC .................... 604/264, 523–532, 95.01–95.05
See application file for complete search history.

(56) References Cited

U.S. PATENT DOCUMENTS

| | | | | |
|---|---|---|---|---|
| 5,308,318 | A * | 5/1994 | Plassche, Jr. | ...... A61M 25/0147 604/540 |
| 7,641,630 | B2 * | 1/2010 | Accisano, III | ...... A61M 25/007 600/585 |
| 7,740,608 | B2 * | 6/2010 | Lampropoulos | .. A61M 25/0097 604/523 |

* cited by examiner

*Primary Examiner* — Phillip Gray

(57) ABSTRACT

An anesthesia delivery device with a syringe receiving chamber, a cannula joint, a thin resilient tubular member, a string member and a string retaining member. The thin tubular member is attached to one end of the syringe receiving chamber. The tubular member includes a plurality of small apertures for allowing anesthesia out to surrounding tissue. The cannula joint is attached at the proximal end of the thin tubular member. A syringe can be attached to the cannula joint. The tubular member includes a pair of opposing tabs that each include an aperture for allowing the string member to pass through to form a loop that can surround the shaft of a tendon harvesting tool. The string member ends can be held in place by the string retaining member. A preferred embodiment includes the thin tubular member is approximately twenty-seven centimeters long and includes a plurality of distance identifying markings.

5 Claims, 6 Drawing Sheets

ANESTHESIA DELIVERY DEVICE

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of surgical accessory tools and more specifically to an anesthesia delivery device.

Anesthesia is extremely important for pain control in medicine. The use of general and local anesthetics along with oral pain medication are the main treatments for pain. It is common to apply local anesthetics before, during and after surgical procedures. The treatment of postoperative pain has allowed patients to return home sooner and decrease their consumption of oral pain medication after discharge. Intraoperative local anesthetics have also allowed for a decrease in the amount of medication needed for general anesthesia.

There are several methods for administering local anesthetics. A technique known as a nerve block will decrease or eliminate pain in the distribution of that nerve. The nerve is blocked proximally resulting in anesthesia distal to the block. If the surgical site is innervated only by that nerve the block is usually complete. One problem commonly encountered is that many surgical sites are innervated by multiple nerves making it difficult to provide complete analgesia with a single nerve block. Local infusion of anesthetics often used to supplement these types of blocks.

It is also common to harvest autologous tissue from another site for use in the surgical procedure, thus necessitating anesthesia at two different surgical sites. Tendons are frequently used as autologous grafts for surgery. Tendons are harvested using minimally invasive techniques, generally by making a small incision near the tendon insertion and "stripping" them out. The tendon harvester is usually a long thin instrument which is passed around the tendon and then pushed up the tendon until the tendon turns into muscle at which point the tendon is cut free. This technique can cause pain over a relative large area which is innervated by several nerves and is oftentimes isolated from the surgical site.

The minimally invasive nature of this harvesting technique poses problems for delivery of local anesthetics to the harvest site. To this date there have been no instruments designed to deliver a local anesthetic to the harvest site at the time of tendon harvesting thus minimizing both intraoperative and postoperative pain. There is therefore a need for an instrument that attaches to the tendon stripper or any other minimally invasive instrument which is placed beneath the skin and will deliver local anesthetic at a site which cannot normally be accessed through the minimally invasive incision.

BRIEF SUMMARY OF THE INVENTION

The primary object of the invention is to provide a device that can deliver a local anesthetic to a tendon site at the time of tendon harvesting.

Other objects and advantages of the present invention wilt become apparent from the following descriptions, taken in connection with the accompanying drawings, wherein, by way of illustration and example, an embodiment of the present invention is disclosed.

In accordance with a preferred embodiment of the invention, there is disclosed an anesthesia delivery device comprising: a syringe receiving chamber, a cannula joint, a thin resilient tubular member, a string member, a string retaining member, said syringe receiving chamber being rigid and cylindrical in shape, said string retaining member located on the side wall of said syringe receiving chamber, said thin tubular member centrally and fixedly attached to one end of said syringe receiving chamber, said thin tubular member being closed at its distal end, said thin tubular member walls including a plurality of small apertures located near the distal end of said thin tubular member, said cannula joint fixedly attached at the proximal end of said thin tubular member and internal to said syringe receiving chamber, said thin tubular member including a pair of opposing tabs located at the distal end, said tabs each including an aperture for allowing said string member to pass through in a sliding fashion, and said string member ends capable of being held firmly in place by said string retaining member.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
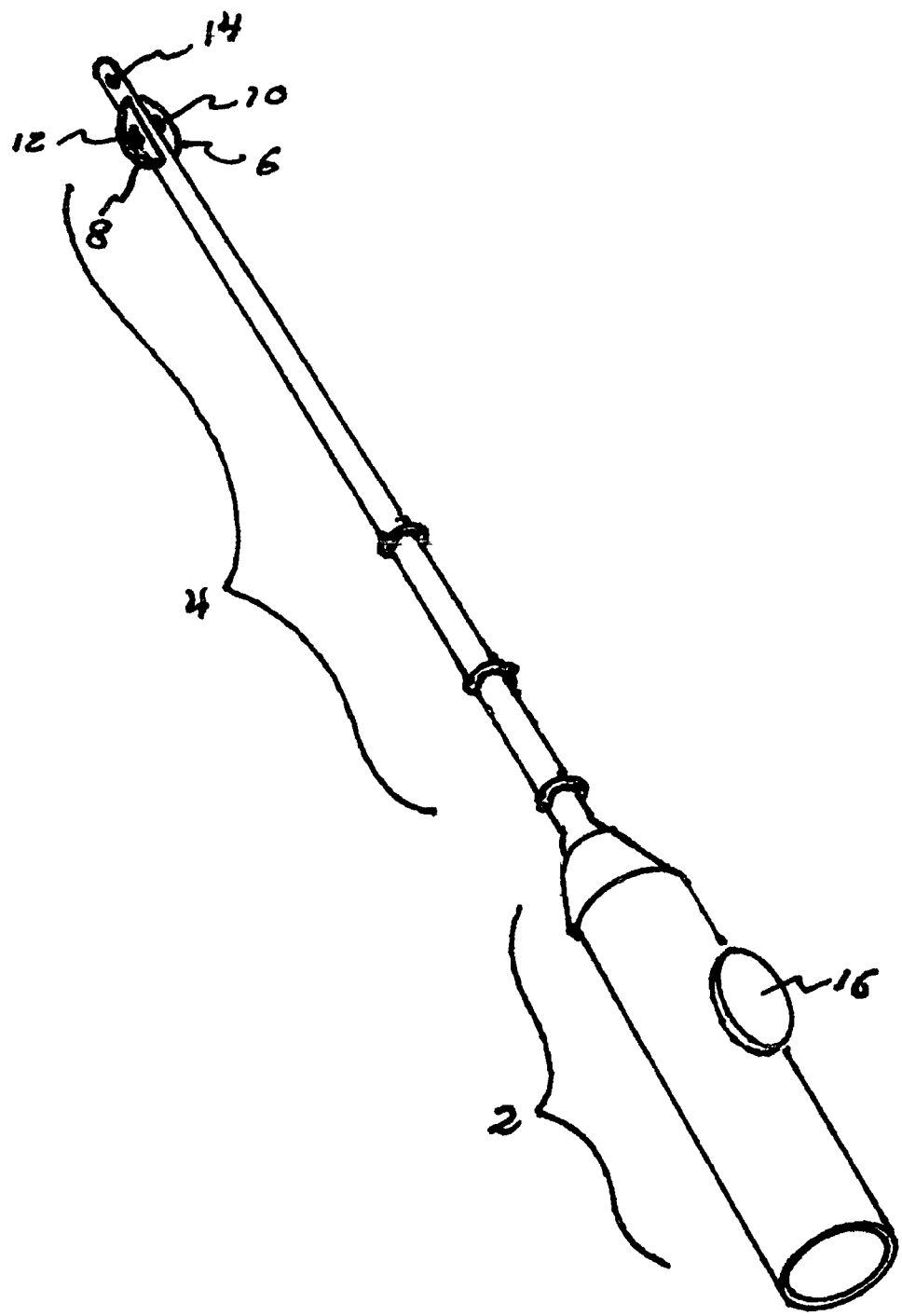
FIG. 1 is a perspective view of the invention.

Referring now to FIG. 1 we see a perspective view of the anesthesia delivery device of the present invention 100. The device 100 consists of a cylindrical chamber 2 and attached thin resilient tube 4. The device 100 is preferably injection molded in one piece from an inert plastic compound such as high density polyethylene. But may be made of other moldable materials and also may be made in two pieces rather than one. The ideal length of the tube 4 is approximately twenty-seven centimeters long, thereby allowing a user to insert the tube 4 approximately twenty-five centimeters into a patient's body part, such as a leg. A pair of opposing tabs 6, 8 protrude from either side of tube 4 near the end of the tube. Small apertures 14 are located axially at the far end of the tube 4 which allow anesthesia liquid to exit. Each tab 6,8 includes an aperture 10, 12 that can accept a string 40 as shown in FIG. 3. The apertures are large enough to let the string 40 slip easily through them. Attached disk shaped knob 16 is a string retainer and will be discussed in more detail below The front end of chamber 2 is open and can accept the insertion a standard disposable syringe 22 shown in dotted lines in FIG. 2.

Figure 2:
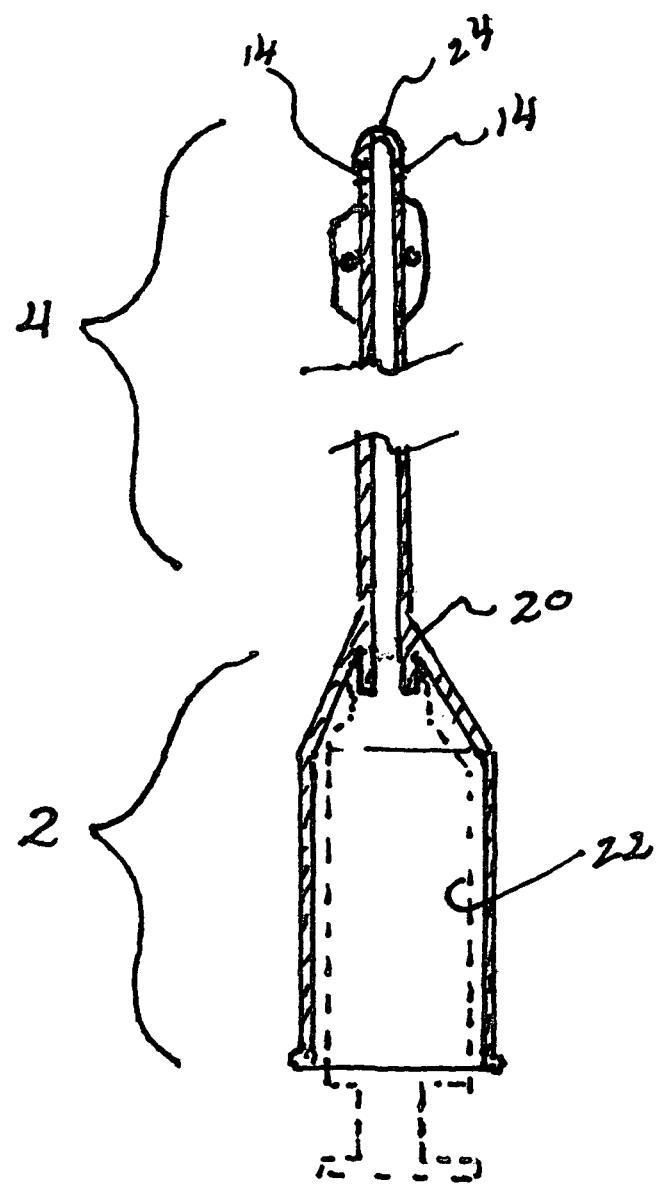
FIG. 2 is a section view of the invention.
Figure 3:
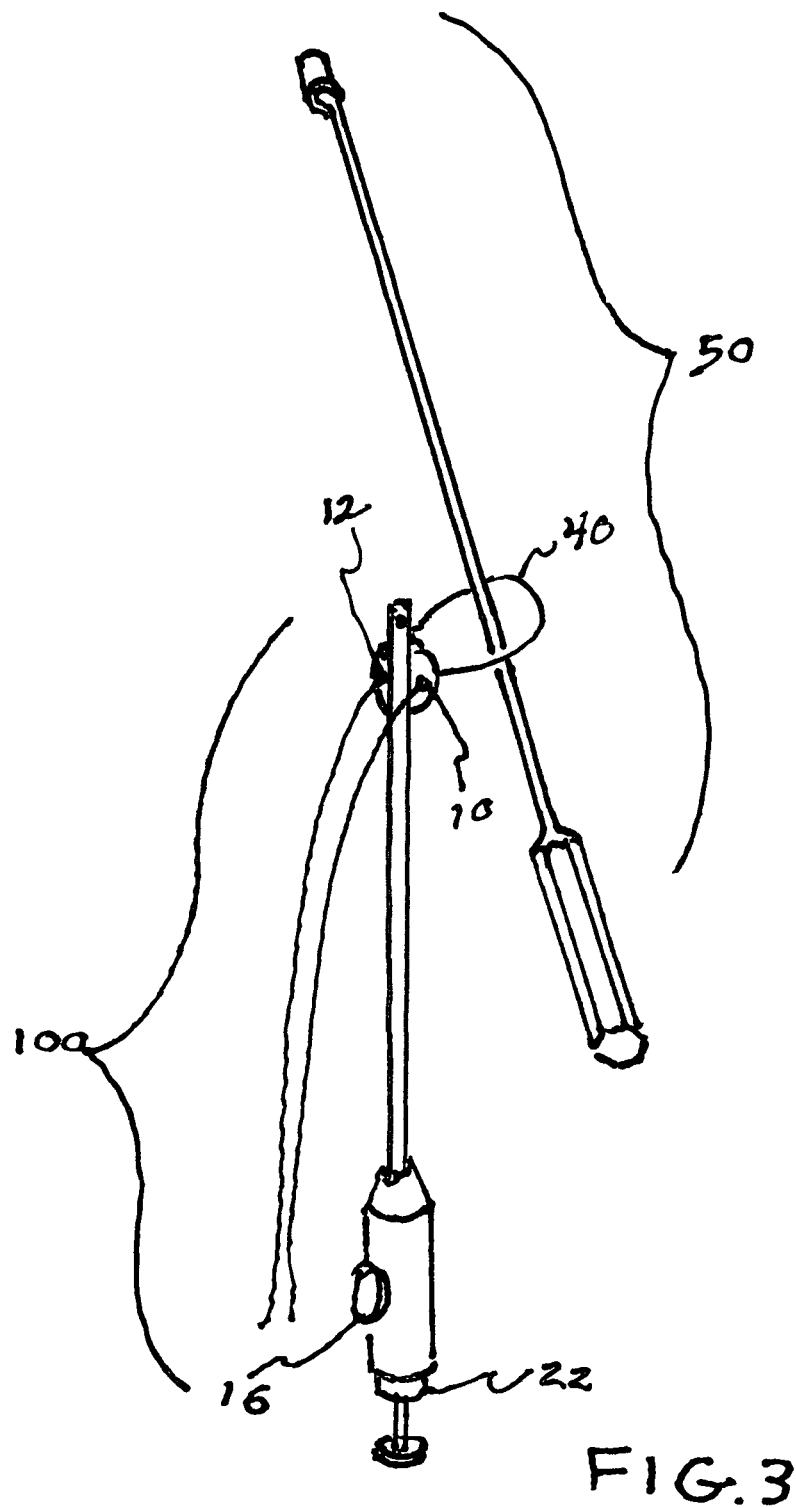
FIG. 3 is a perspective view of the invention being attached to a tendon harvesting tool.

FIG. 2 is a side section view that longitudinally bisects the invention 100. A cannula such as a Luer type connection is molded into the far end of the syringe holding chamber 2 and at the start of the thin tube member 4. This allows the user to insert and physically connect the tip of a standard syringe 22, shown in dotted lines, to the invention 100. The length of the cylinder 2 is less than the length of a standard sixteen ml syringe body. The inside diameter of cylinder 2 is larger than the outside diameter of a standard twenty ml syringe. In this way, the present invention 100 can be used with either a sixteen or a twenty ml syringe as determined by the user. Apertures 14 can be clearly seen near the closed tip 24 of the tube 4. Anesthesia type liquid is stored inside syringe 22 and can be injected into tube 4 and finally out of apertures 14 and into the tissue of a patient who is undergoing a tendon extraction.

FIG. 3 is a perspective view of a tendon stripping tool 50 and the present invention 100. The user first inserts the tendon stripping tool 50 into the patient and slides the tool up to the beginning point of the tendon, where the tendon reaches muscle. After the tool 50 is inserted the user forms a loop around the shaft of tool 50 with string 40 by inserting the string into the two apertures 10, 12 as shown. The user Then pulls on the string ends to draw the thin tube 4 of the present invention to be in close proximity to the rod of the tendon stripping tool 50. The end portions of the string 40 are then secured to string retaining member 16. The user then slides the tube 4 of the present invention along side of the rod of the tendon stripping tool, thereby using the same tunnel that has been created by the tendon stripping tool 50 as it was inserted into the patient's leg as shown in FIG. 3.

Figure 4:
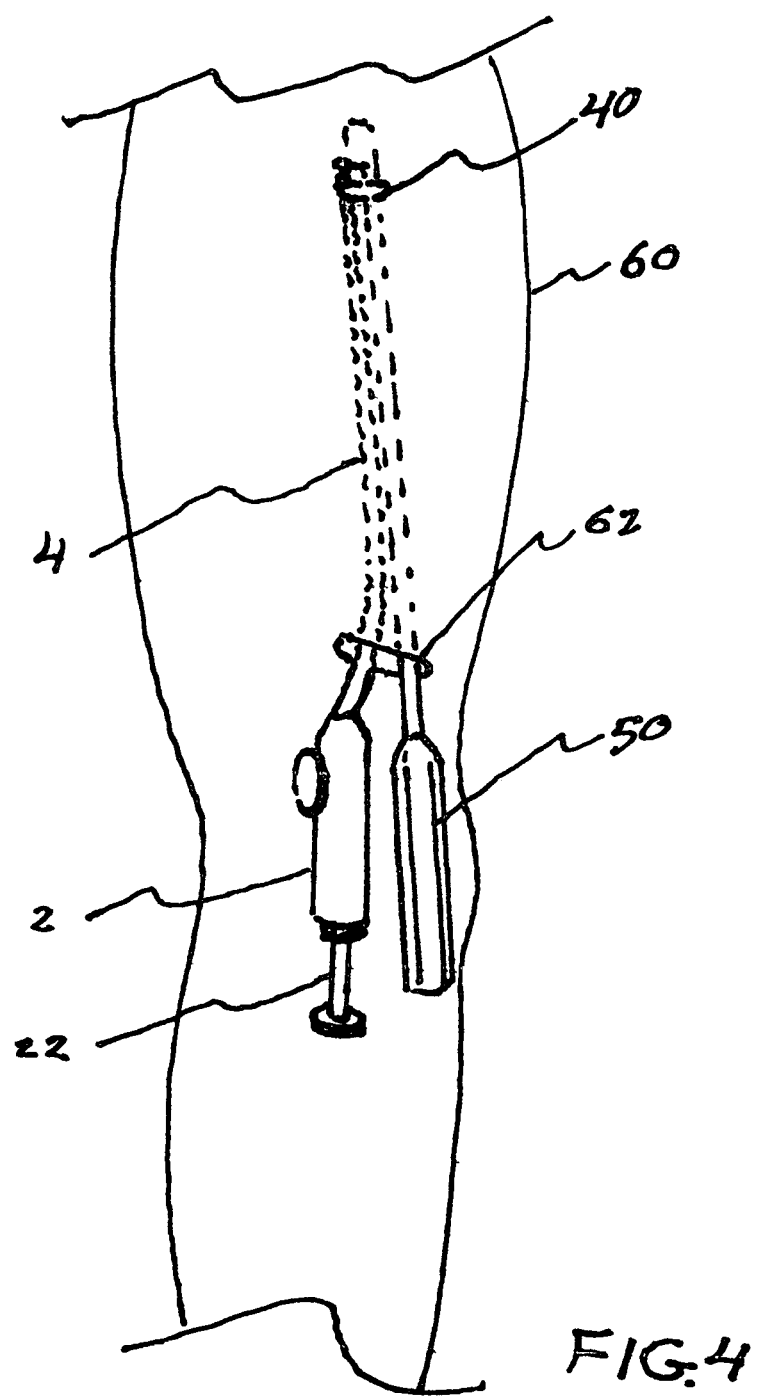
FIG. 4 is a perspective view of the invention in use.

FIG. 4 is a perspective view of both the present invention 100 and the tendon stripping tool 50 after they have both been inserted into the patient's leg 60. The user can now inject a liquid anesthesia by pressing on syringe 22 plunger which causes the liquid to exit ports 14 and to anesthetize the tissue that is in close proximity to the tendon that is being cut by the tendon stripping toot 50.

Figure 5:
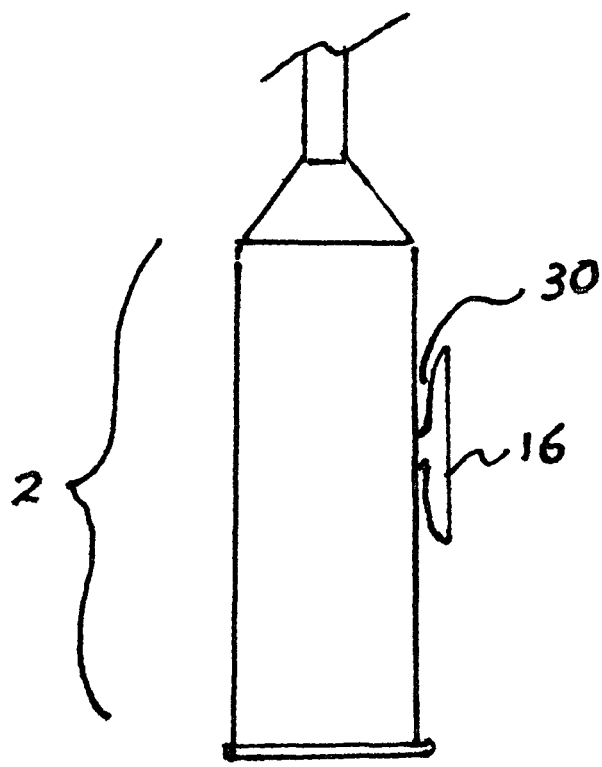
FIG. 5 is a partial side view showing the string retaining member.

FIG. 5 is a side view of the syringe holding chamber 2 clearly showing the string retaining member 16. The string 40 can be trapped and temporarily retained in the tapered space between the underside of the string retaining member 16 and the outer surface of the syringe holding chamber 2.

Figure 6:
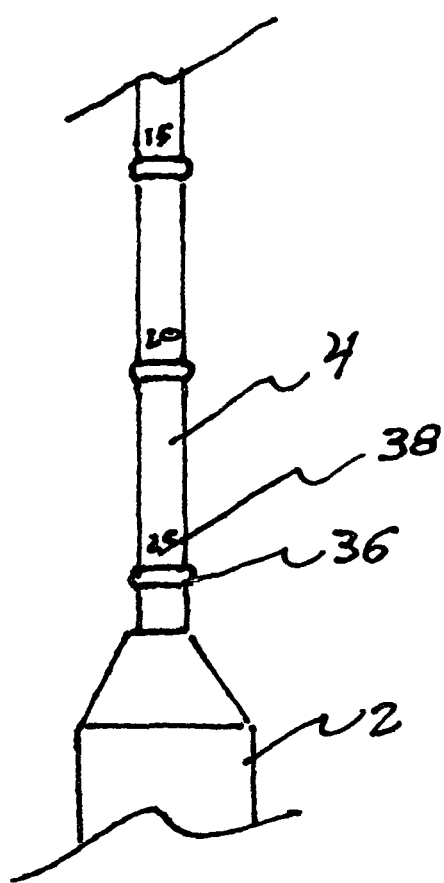
FIG. 6 is a partial side view showing distance indicators on thin tube.

FIG. 6 is a partial side view of the thin tube 4 portion of the present invention 100. A plurality of protruding rings 36 and distance indicating numbers 38 help the user know how deep he or she has inserted the tube 4 into the patient's leg, or other body part.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. An anesthesia device comprising:
   a syringe receiving chamber;
   a cannula joint;
   a thin resilient tubular member;
   a string member;
   a string retaining member;
   said syringe receiving chamber being rigid and cylindrical in shape
   said string retaining member located on the side wall of said syringe receiving chamber;
   said thin tubular member centrally and fixedly attached to one end of said syringe receiving chamber;
   said thin tubular member being closed at its distal end;
   said thin tubular member walls including a plurality of small apertures located near the distal end of said thin tubular member;
   said cannula joint fixedly attached at the proximal end of said thin tubular member and internal to said syringe receiving chamber;
   said thin tubular member including a pair of opposing tabs located at the distal end;
   said tabs each including an aperture for allowing said string member to pass through in a sliding fashion; and
   said string member ends capable of being held firmly in place by said string retaining member.

2. An anesthesia device as claimed in claim 1 wherein said thin tubular member is approximately twenty-five centimeters long and includes a plurality distance identifying markings.

3. An anesthesia device as claimed in claim 1 wherein said cannula joint is a Luer joint and accepts a standard disposable syringe.

4. An anesthesia device as claimed in claim 1 wherein said syringe receiving chamber has a wide enough inside diameter to accept a twenty mm syringe and is short enough in length so that the barrel and plunger end of a sixteen mm syringe can protrude out slightly.

5. An anesthesia device as claimed in claim 1 further comprising the steps of filling a syringe with anesthetic fluid;
   inserting said syringe into said syringe receiving chamber and joining the tip of said syringe to said thin tube member via said cannula joint;
   creating a loop from said string member by passing said string through said apertures in said thin tube tabs;
   surrounding the shaft of a tendon harvesting tool with said loop of said string member and then pulling the said string member so that said thin tube member of said anesthesia device is in close parallel proximity to said tendon harvesting tool shaft and holding said string member in place by wrapping said string member around said string retaining member;
   sliding said thin tubular member up along side of the shaft of said tendon harvesting tool while said tendon harvesting tool is already inserted into a patient's body;
   and injecting said anesthetic liquid via said attached syringe through said thin tubular member and out of said apertures located near the distal end of said thin tube member.

* * * * *